United States Patent [19]

Shankar et al.

[11] Patent Number: 5,155,242
[45] Date of Patent: Oct. 13, 1992

[54] PROCESS FOR STARTING-UP AN ETHYLENE OXIDE REACTOR

[75] Inventors: Pettai K. Shankar, Sugarland; Jitendra G. Patel, Katy; Beamon M. Johnson, Brookshire, all of Tex.

[73] Assignee: Shell Oil Company, Houston, Tex.

[21] Appl. No.: 802,574

[22] Filed: Dec. 5, 1991

[51] Int. Cl.$^5$ .......................... C07D 301/10
[52] U.S. Cl. .................... 549/534; 502/347
[58] Field of Search ......................... 549/534

[56] References Cited

U.S. PATENT DOCUMENTS

| | | | |
|---|---|---|---|
| 2,194,602 | 3/1940 | Law et al. | 549/534 |
| 2,219,575 | 10/1940 | McNamee et al. | 549/534 |
| 2,279,469 | 4/1942 | Law et al. | 549/534 |
| 2,279,470 | 4/1942 | Law et al. | 549/534 |
| 2,765,283 | 10/1956 | Sacken | 549/534 |
| 3,962,136 | 6/1976 | Nielsen et al. | 252/454 |
| 4,010,115 | 3/1977 | Nielsen et al. | 252/454 |
| 4,810,689 | 3/1987 | Hayden | 549/534 |
| 4,822,900 | 4/1989 | Hayden | 549/534 |
| 4,831,162 | 5/1989 | Nakajima | 549/534 |
| 4,874,879 | 10/1989 | Lauritzen et al. | 549/536 |
| 4,950,773 | 8/1990 | Monnier et al. | 549/534 |

Primary Examiner—Joseph E. Evans

[57] ABSTRACT

This invention relates to a process for starting up a fixed bed ethylene oxide reactor containing a supported silver catalyst promoted with one or more alkali metal promoter(s) which involves heating the reactor to slightly below normal operating conditions, passing an ethylene containing gas over the catalyst, adding a chlorohydrocarbon moderator to the gas passing over the catalyst and after approximately 0.1-5 milliliters of moderator (basis liquid) per cubic foot of catalyst has been added, then adding oxygen to the gas passing over the catalyst to initiate the ethylene oxidation reaction and subsequently raising the reactor temperature and gas flow rates to operating conditions.

16 Claims, 1 Drawing Sheet

PROCESS FOR STARTING-UP AN ETHYLENE OXIDE REACTOR

FIELD OF THE INVENTION

This invention relates to a process for starting-up a fixed bed ethylene oxide reactor containing a catalyst consisting essentially of silver and one or more alkali metal promoter(s) supported on an alpha alumina carrier.

BACKGROUND OF THE INVENTION

A number of commercial ethylene oxide processes utilize a tubular reactor for converting ethylene to ethylene oxide. This fixed bed reactor typically utilizes a silver-based catalyst which has been supported on a porous support and which is typically promoted with one or more alkali metal promoter(s). The shell side of the ethylene oxide reactor typically utilizes a high temperature coolant to remove the heat generated by the oxidation reaction. Under operating conditions a chlorohydrocarbon moderator is utilized to control the oxidation reaction. Reactor product gases are passed through an ethylene oxide absorber and the overhead gases from the absorber, containing unreacted ethylene and ballast gas such as methane and other inerts are recycled back to the reactor with some carbon dioxide and inerts in the overhead stream being removed on the way back to the reactor.

The usual practice for starting up fresh silver/alkali metal-supported ethylene oxide catalysts in a commercial plant is to first add ethylene and diluent gas; then slowly introduce oxygen to get the reaction started; and then to gradually introduce chlorohydrocarbon moderator to control the reaction after it is producing enough heat to become self-sustaining. For the traditional silver-based, alkali-metal promoted supported catalyst, the chlorohydrocarbon moderator serves to decrease the activity (i.e., raise the temperature as required to obtain a given conversion level) while increasing selectivity to ethylene oxide. When utilizing conventional alkali metal-promoted, supported silver catalysts, the catalysts are very active at normal start-up temperatures. Chlorohydrocarbon moderator levels are introduced after start-up to control the high catalyst activity to reduce the conversion level, and to prevent a "run away".

The appearance of a new generation of ethylene oxide catalysts comprising silver/rhenium/alkali metal supported on alumina has presented start-up considerations considerably different than those presented by the conventional silver/alkali metal catalysts. As is illustrated in FIG. 1, the rhenium-containing catalysts have a completely opposite activity response to the presence of chloride-containing moderator than do the conventional catalysts. The rhenium-containing catalysts have an initial low activity, requiring a very high reactor temperature (as measured by the reactor coolant temperature) to operate properly. Since most commercial reactors cannot reach this required high temperature during start-up, special techniques have been evolved. U.S. Pat. No. 4,874,879, issued Oct. 17, 1989, discloses a method of prechloriding these rhenium-containing catalysts to enhance their activity and allow start-up at low temperatures. The prechloriding enhances the initial activity of the rhenium-containing catalyst. There is no indication in this patent that such prechloriding allows for a faster start-up or enhances the life of such rhenium-containing catalyst.

It has been found that the application of a prechloriding technique to the conventional silver/alkali metal-promoted alumina-supported catalyst, while decreasing the activity of the catalyst, allows for a faster start-up of the reactor, thus providing a significant cost advantage as well as extending the life of the catalyst.

SUMMARY OF THE INVENTION

This invention relates to a process for starting up a fixed bed ethylene oxide reactor containing a catalyst consisting essentially of silver and one or more alkali metal promoter(s) supported on an alumina carrier which process comprises a) heating the reactor to slightly below its normal operating temperature, b) passing an ethylene-containing gas over the catalyst, c) adding a chlorohydrocarbon moderator to the gas passing over the catalyst and after an amount of moderator containing the chlorine equivalent found in about 0.1 to about 5 milliliters (basis liquid) of ethylene chloride per cubic foot of the catalyst has been added, d) adding oxygen to the gas passing over the catalyst to start the oxidation reaction and raising the reactor temperature and gas flow rates to operating conditions. This process is applied to new or fresh catalysts, as well as to used catalysts that have been subjected to a prolonged shutdown period.

DESCRIPTION OF THE PREFERRED EMBODIMENT

Catalyst

Figure 1:
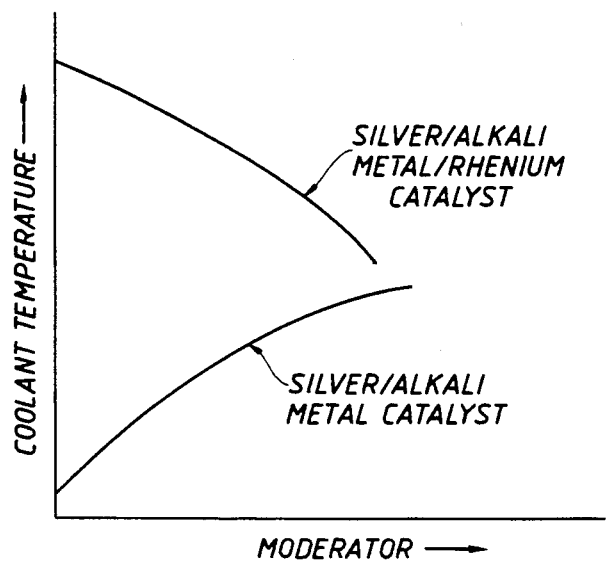
FIG. 1 illustrates the activity response as a function of chlorohydrocarbon moderator present in a reactor of the silver/alkali metal supported catalysts used in this invention and of the silver/rhenium/alkali metal supported catalysts of the prior art.

The catalyst that is used in the fixed bed reactor that is started up by the process of the instant invention consists essentially of silver and one or more alkali metal promoter(s) supported on an alumina carrier, preferably an alpha alumina carrier. Typical of these catalysts are those described in U.S. Pat. No. 3,962,136, issued June 8, 1976 and U.S. Pat. No. 4,010,115, issued Mar. 1, 1977.

The catalysts used in the instant process comprise a catalytically effective amount of silver and a promoting amount of one or more alkali metal(s). Preferably the major amount of alkali metal promoter present is a higher alkali metal selected from potassium, rubidium, cesium and mixtures thereof. Most preferably the major amount of alkali metal is cesium. Combinations of alkali metals, such as cesium and lithium are quite suitable. Minor amounts of sodium and/or lithium may also be present. Concentrations of alkali metal (measured as the metal) between about 10 and 3000 ppm, preferably between about 15 and about 2000 ppm and more preferably between about 20 and about 1500 ppm by weight of total catalyst are desirable.

The Process

The process of the instant invention is applied to new catalysts as well as to aged catalysts that, due to a plant shut-down, have been subjected to a prolonged shut-in period.

When new catalysts are utilized it has been found useful to subject these catalysts to a high temperature treatment with nitrogen gas passing over the catalyst. The high temperature treatment converts a significant portion of the organic nitrogen-containing compounds used in the manufacture of the catalyst to nitrogen-containing gases which are swept up in the nitrogen stream and removed from the catalyst.

Typically, the catalyst is loaded into the tube reactor and by utilizing a coolant heater, the temperature of the reactor (as measured by the coolant temperature) is brought up to within 10° F. to 100° F. (6° C. to 56° C.), preferably to 20° F. to 50° F. (11° C. to 28° C.) below the normal operating temperature. Temperatures closer to the normal operating temperatures can be utilized, but in most cases the lower temperatures are adequate for the chloride pretreatment and subsequent start-up. In general, the reactor is heated to a temperature between about 350° F. (177° C.) and 475° F. (246° C.). For aged catalysts the reactor is heated to the upper temperature range, say between about 420° F. (216° C.) and 475° F. (246° C.).

A nitrogen flow, if utilized, is then passed over the catalyst at a flow rate typically above about 5 percent of the design flow rate, preferably above about 15 percent of the design flow rate, up to the full design flow rate. The nitrogen flow may be initiated before or during reactor heatup. The nitrogen gas is typically passed over the catalyst for a period of time ranging from about ½ of a day to about 7 days, preferably from about 1 to about 3 days. During this purge time the nitrogen stream is monitored for nitrogen-containing decomposition products from the catalyst. The start-up of used catalysts may or may not require the use of nitrogen, but it is frequently used. When nitrogen is not utilized, the reactor may be pressurized with ethylene, methane or other non-oxidizing gas.

After the nitrogen-containing decomposition products have been removed to a suitable low level, generally less than about 10 ppm, the recycle loop to the ethylene oxide reactor is then pressurized with ethylene and a suitable ballast gas such as methane or nitrogen in preparation for start-up. Concentrations of ethylene in the recycle loop are normally maintained at levels of about 5-20% mol. A gas flow rate above about 5 percent of design rate, preferably above about 15 percent of design rate, up to the full design rate, is maintained over the reactor. For those few commercial reactors that operate with once through flow without recycle, the flow rates typically will be at full design flow rates, with ethylene levels at about 5-20% mol.

A chlorohydrocarbon moderator is then added to the recycle gas stream being fed to the ethylene oxide reactor. The amount of chlorohydrocarbon moderator is added slowly over a period of several hours until an amount of chlorohydrocarbon moderator equivalent, based on the chloride content, to approximately 0.1 to about 5 milliliters, preferably 0.5 to about 2 milliliters and most preferably 1 to about 1.5 milliliters of liquid ethyl chloride per cubic foot of catalyst in the reactor bed has been added to the gas stream being fed to the reactor.

Suitable chlorohydrocarbons used as moderators comprise the $C_1$ to $C_8$ chlorohydrocarbons, that is compounds comprising hydrogen, carbon and chlorine. Preferably these chlorohydrocarbons are $C_1$ to $C_4$ chlorohydrocarbons and most preferably they are $C_1$ and $C_2$ chlorohydrocarbons. The chlorohydrocarbons may be optionally substituted with fluorine. Illustrative examples of these moderators include methyl chloride, ethyl chloride, ethylene dichloride, vinyl chloride and mixtures thereof. Preferred moderators are ethyl chloride, ethylene dichloride and vinyl chloride, particularly ethyl chloride.

Ethyl chloride, which is the preferred chlorohydrocarbon moderator, is used as the basis for calculating the amount of moderator that is to be passed over the catalyst. When a different moderator is to be used, the amounts can be calculated from the ethyl chloride amounts provided herein by adjusting for the differences in liquid densities and gram equivalent weights, basis chlorine, between ethyl chloride and such different moderator.

The moderator is added to the reactor during the prechloriding step preferably during a period of time ranging from about 0.5 to about 15 hours. These times, however, are not critical and shorter or longer periods can be used.

During the prechlorination process, chloride contents (basis ethyl chloride) in the recycle are typically maintained in the range of about 1-10 ppmv and the reactor is maintained at a temperature between about 350° F. (177° C.) and 475° F. (246° C.). Typically the reactor temperature during the prechlorination process will be maintained at about 10° F. to 100° F. (6° C. to 56° C.), preferably to 20° F. to 50° F. (11° C. to 28° C.) below the normal operating temperature.

After the chlorohydrocarbon moderator has been fed to the catalyst in the above-specified amounts, oxygen is then added to the recycle feed stream at initially above about 5% of design rate, preferably above about 15% of design rate, up to the full design rate. Reaction initiation will occur within a few minutes of the addition of the oxygen, after which point the oxygen feed to the reactor, the feed gas to the reactor and the reactor temperature are raised to approximately the design conditions over a period of time ranging from about 24 hours to about 60 hours.

For purposes of illustration, the following Table 1 shows the range of operating conditions for which commercial ethylene oxide reactors units are designed.

TABLE 1

|  | Broad | Preferred |
|---|---|---|
| *GHSV, hour$^{-1}$ | 1550–10000 | 2500–8000 |
| Inlet pressure, psig | 150–400 | 200–350 |
| Inlet Feed, % mol |  |  |
| ethylene | 1–40 | 10–35 |
| $O_2$ | 3–12 | 6–10 |
| $CO_2$ | 2–40 | 3–15 |
| ethane | 0–3 | 0–3 |
| Ballast (methane and/or nitrogen) | Balance | |
| chloro-moderator, ppmv total | 0.1–20 | 0.5–15 |
| Coolant temperature, °C. | 175–315 | 205–290 |
| Catalyst temperature, °C. | 185–325 | 215–300 |
| $O_2$ conversion level, % | 10–60 | 20–60 |
| EO Production (Work Rate, lbs. of EO or its equivalent/cu. ft. of catalyst per hour) | 2–25 | 5–20 |

*Liters of gas at standard temperature and pressure passing over one liter of packed catalyst per hour.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The following example is provided as a means to illustrate the process of the instant invention and is not to be construed as limiting the invention.

EXAMPLE

In the following example reactor A represents a fixed bed tubular ethylene oxide reactor with recycle loop to which the prechloriding technique of this process was applied. Reactor B represents the same type of reactor which was started up in a conventional fashion without the application of the prechloriding technique of this invention. The following description describes the treatment of Reactors A and B prior to start-up.

An alumina-supported silver catalyst containing cesium as a promoter was loaded into the reactor. The reactor was then subjected to a nitrogen heat treatment to remove ammonia and amines from the fresh catalyst. The reactor was heated to about 420°–430° F. (216°–221° C.) utilizing the reactant coolant heater during which heat-up nitrogen gas was circulated through the recycle loop. Nitrogen flow was continued for about 70 hrs., at which point the ammonia concentration fell below 10 ppmv.

After removal of the nitrogen-containing compounds from the catalyst, the reactor recycle loop was pressurized with ethylene and nitrogen in preparation for prechloriding and/or start up. A gas flow rate of approximately design flow rate was maintained in the reactor and the ethylene concentration was controlled at about 10% v.

Reactor A Prechloriding and Start-Up

Ethyl chloride was then added to the inlet of reactor A at a rate of about 150 milliliters per hour. The reactor temperature was controlled at about 370°–380° F. (188°–193° C.) The chloride concentration in the recycle loop increased rapidly and stabilized at about 8-9 ppmv. The prechloriding of the reactor was continued for about 6 hours, at which point about 1.2 milliliters of liquid ethyl chloride per cubic foot of catalyst had been added to the reactor. Ethylene concentration then was brought up to about 15% mol.

The reactor was then started up by adding oxygen to the reactor, adjusting the ethyl chloride level to provide a concentration of about 1 ppmv in the recycle loop and raising the temperature. The ethylene oxide reaction started at about 405° F. (207° C.) and about 1% v oxygen. Temperature, chloride levels and oxygen concentrations were adjusted over the next 60 hours to bring the reactor to design operating levels.

Reactor B Start-Up

Reactor B was started up by adding oxygen to the reactor gases of nitrogen and ethylene, and increasing the temperature. The ethylene oxide reaction started at about 390° F. (199° C.). Ethyl chloride was then started at a rate of about 100 milliliters per hour, gradually lowering the rate to maintain about 1 ppmv of chloride in the recycle loop. Temperature, chloride levels and oxygen concentrations were adjusted over the next 100 hours to bring the reactor to design operating levels which were the same as in Reactor A.

Test Comparisons

As noted above, the prechlorination step of the instant process allowed Reactor A to be brought up to design operating levels in about 60 hours; whereas, it took about 100 hours to bring the non-prechlorided Reactor B to the same design operating levels. Thus, the instant process shortened the normal start-up time by about 40 hours, thereby providing a significant commercial advantage. In a large scale commercial operation, shortening the start-up process by several days can be worth several hundreds of thousands of dollars to the plant operator.

Figure 2:
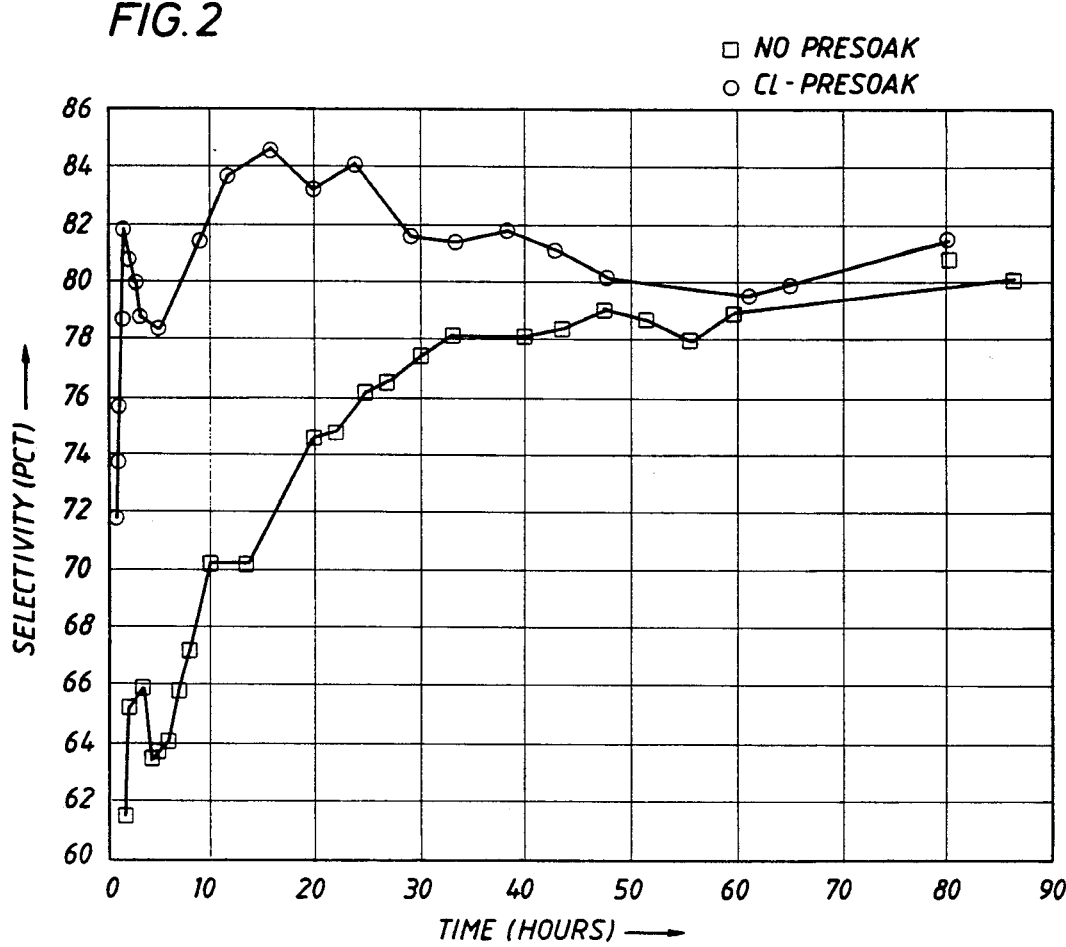
FIG. 2 illustrates the selectivity response of silver/alkali metal-promoted alumina-supported catalysts as a function of time after start-up which either have or have not been subjected to the prechloriding treatment of this invention.

The ethylene oxide selectivity (moles of ethylene oxide produced/moles of ethylene consumed) was measured during the start-up as a function of time. These results are shown in FIG. 2 for the start-up process of this invention and a conventional start-up process. As can be seen from this Figure, the instant process allowed optimum selectivities to be reached in about a third of the time of that required by the conventional process.

Oxygen conversions were also measured during start-up. During steady operations oxygen conversion levels will normally be held at about 30–40%. However, during conventional start-up, due to the high activity of the catalyst, the oxygen conversions will initially overshoot design limits. Extremely high oxygen conversions can result in hot spots in the catalyst which can decrease its life due to sintering. The start-up procedure of the instant process results in peak oxygen conversion levels during start-up some 30% lower than the conventional start-up. This damping of the start-up oxygen conversions will, it is believed, contribute to a longer life for the catalyst.

What is claimed is:

1. A process for starting up a fixed bed ethylene oxide reactor containing a catalyst consisting essentially of silver and one or more alkali metal promoter(s) supported on an alumina carrier, which process comprises:
   a) heating the reactor to a temperature between about 350° F. and 475° F.,
   b) passing an ethylene-containing gas over the catalyst in the reactor,
   c) adding a chlorohydrocarbon moderator to the gas passing over the catalyst and after an amount of moderator containing the chlorine equivalent found in about 0.1 to about 5 milliliters (basis liquid) of ethyl chloride per cubic foot of the catalyst has been added, then
   d) adding oxygen to the gas passing over catalyst, and adjusting the reactor temperature and gas flow rates to operating design conditions.

2. The process of claim 1 wherein in step b) the ethylene-containing gas is passed over the reactor at a flow rate above 5 percent of the design flow rate.

3. The process of claim 2 wherein in step b) the ethylene-containing gas is passed over the reactor at a flow rate above 15 percent of the design flow rate.

4. The process of claim 1 wherein in step b) the ethylene-containing gas also contains nitrogen or methane.

5. The process of claim wherein the chlorohydrocarbon moderator is a $C_1$ to $C_8$ chlorohydrocarbon.

6. The process of claim 5 wherein the chlorohydrocarbon moderator is a $C_1$ to $C_4$ chlorohydrocarbon.

7. The process of claim 6 wherein the chlorohydrocarbon moderator is a $C_1$ or $C_2$ chlorohydrocarbon.

8. The process of claim 7 wherein the chlorohydrocarbon moderator is selected from the group consisting of methyl chloride, ethyl chloride, ethylene dichloride, vinyl chloride and mixtures thereof.

9. The process of claim 8 wherein the chlorohydrocarbon moderator is ethyl chloride.

10. The process of claim 1 wherein in step c) from about, 0.5 to about 2 milliliters of moderator per cubic feet of catalyst been added.

11. The process of claim 10 wherein from about 1 to about 1.5 milliliters of moderator per cubic feet of catalyst has been added.

12. The process of claim 1 wherein in step c) the moderator is added over a period of time ranging from about 0.5 to about 15 hours.

13. The process of claim 1 wherein in step c) the moderator is added at a rate sufficient to maintain a concentration of about 1-10 ppmv in the gas passing over the catalyst.

14. The process of claim 1 wherein in step d) the reactor temperature and gas flow rates are raised to operating conditions over a period of time after the start of the oxygen addition ranging from about 24 hours to about 60 hours.

15. The process of claim 1 wherein nitrogen gas is passed over the catalyst prior to passing ethylene-containing gas of step b) over the catalyst.

16. The process of claim 15 wherein the nitrogen is passed over the catalyst for a period of time ranging from about $\frac{1}{2}$ to about 7 days.

* * * * *